US011013475B2

(12) United States Patent
Hunt et al.

(10) Patent No.: US 11,013,475 B2
(45) Date of Patent: May 25, 2021

(54) METHODS AND SYSTEMS FOR SYNTHETIC COMPUTED TOMOGRAPHY (CT) IMAGE CREATION (71) Applicant: Memorial Sloan Kettering Cancer Center, New York, NY (US)

(72) Inventors: Margie A. Hunt, New York, NY (US); Joseph Owen Deasy, New York, NY (US); Reza Farjam, New York, NY (US); Aditya Apte, New York, NY (US); Neelam Tyagi, New York, NY (US); Harini Veeraraghavan, New York, NY (US); Kristen L. Zakian, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/348,181

(22) PCT Filed: Nov. 10, 2017

(86) PCT No.: PCT/US2017/061038
§ 371 (c)(1),
(2) Date: May 8, 2019

(87) PCT Pub. No.: WO2018/089755
PCT Pub. Date: May 17, 2018

(65) Prior Publication Data
US 2019/0365335 A1    Dec. 5, 2019

Related U.S. Application Data (60) Provisional application No. 62/469,140, filed on Mar. 9, 2017, provisional application No. 62/445,937, filed
(Continued)

(51) Int. Cl.
*G06K 9/00* (2006.01)
*A61B 6/03* (2006.01)
(Continued)

(52) U.S. Cl.
CPC ............ *A61B 6/032* (2013.01); *A61B 6/5247* (2013.01); *A61N 5/103* (2013.01);
(Continued)

(58) Field of Classification Search
CPC . G06T 2207/10088; G06T 2207/20128; G06T 7/11; G06T 2207/30016;
(Continued)

(56) References Cited

U.S. PATENT DOCUMENTS

2007/0038058 A1* 2/2007 West ...................... A61B 90/36
600/407
2010/0329529 A1* 12/2010 Feldman .............. G06K 9/4619
382/131
(Continued)

FOREIGN PATENT DOCUMENTS

WO    WO-2009/109874 A1    9/2009
WO    WO-2018/089753 A2    5/2018
WO    WO-2018/089755 A1    5/2018

OTHER PUBLICATIONS

Burgos, N. et al., Attenuation Correction Synthesis for Hybrid PET-MR Scanners: Application to Brain Studies, IEEE Transactions on Medical Imaging, 33(12):2332-2341 (2014).
(Continued)

*Primary Examiner* — Alex Kok S Liew
(74) *Attorney, Agent, or Firm* — William R. Haulbrook; Margo R. Monroe; Choate, Hall & Stewart LLP (57) ABSTRACT Described herein are systems and methods for synthetic CT image creation that allow MR-only radiotherapy of cancer patients, e.g., head and neck (H&N) cancer patients, prostate
(Continued)

cancer patients, patients with cancer of the pelvis, abdomen cancer patients, patients with cancer of the extremities, brain cancer patients, or thorax cancer patients. The methods and systems described herein feature image processing techniques that improve the similarity between CT and MR images prior to CT-MR image registration, as well as standardization of the MR intensity histograms prior to MR-MR registration. Application of the techniques result in more accurate assignment of the Hounsfield unit to each point in the synthetic CT compared to other atlas-based methods, providing for more accurate dosing in MR-only radiotherapy simulation and planning.

19 Claims, 3 Drawing Sheets

Related U.S. Application Data on Jan. 13, 2017, provisional application No. 62/420,499, filed on Nov. 10, 2016.

(51) Int. Cl.
| | |
|---|---|
| *G06T 7/30* | (2017.01) |
| *A61B 6/00* | (2006.01) |
| *A61N 5/10* | (2006.01) |
| *G01R 33/56* | (2006.01) |
| *G06T 5/50* | (2006.01) |

(52) U.S. Cl.
CPC ............ *G01R 33/5608* (2013.01); *G06T 7/30* (2017.01); *G06T 5/50* (2013.01); *G06T 2207/10081* (2013.01); *G06T 2207/10088* (2013.01)

(58) Field of Classification Search
CPC ......... G06T 2207/10081; G06T 7/0012; G06T 2207/10104; G06T 7/143; G06T 7/149; G06T 2207/30004; G06T 7/0014; G06T 2207/30008; G06T 2207/10132; G06T 2207/20076; G06T 7/174; G06T 7/33; G06T 2207/20156; G06T 7/187; G06T 11/008; G06T 2207/10072; G06T 2207/10092; G06T 2207/10108; G06T 2207/20081; G06T 5/50; G06T 2207/10116; G06T 2207/10136; G06T 2207/20221; G06T 2207/30024; G06T 2207/30048; G06T 2210/41; G06T 7/12; G06T 7/344; G06T 11/006; G06T 2207/20056; G06T 2211/424; G06T 11/00; G06T 11/003; G06T 15/00; G06T 2207/10; G06T 2207/20021; G06T 2207/20041; G06T 2207/20124; G06T 2207/20161; G06T 2207/20208; G06T 2207/30056; G06T 2207/30061; G06T 2207/30088; G06T 2207/30168; G06T 2207/30241; G06T 5/007; G06T 5/008; G06T 5/009; G06T 7/248; G06T 7/251; G06T 7/30; G06T 7/337; G06T 7/60; G06T 7/70; G06T 7/75; G06T 2200/04; G06T 7/0081
See application file for complete search history.

(56) References Cited

U.S. PATENT DOCUMENTS

| | | | | |
|---|---|---|---|---|
| 2012/0112751 | A1* | 5/2012 | Littmann | ........... G01R 33/4838 |
| | | | | 324/322 |
| 2013/0034203 | A1* | 2/2013 | Wang | ..................... A61B 6/508 |
| | | | | 378/41 |
| 2014/0219548 | A1* | 8/2014 | Weis | ..................... A61B 6/025 |
| | | | | 382/154 |

OTHER PUBLICATIONS

Dowling, J.A. et al, An Atlas-Based Electron Density Mapping Method for Magnetic Resonance Imaging (MRI)-Alone Treatment Planning and Adaptive MRI-Based Prostate Radiation Therapy, International Journal of Radiation Oncologybiologyphysics, 83(1):e5-e11 (2012).
Hill, D. L. G. et al., Medical image registration, Physics in Medicine and Biology, 46(3):R1-R45 (2001).
International Partial Search Report, PCT/US2017/061038 (Methods and Systems for Synthetic Computed Tomography (CT) Image Creation, filed Nov. 10, 2017), ISA/EPO, 3 pages, dated Feb. 27, 2018.
International Provisional Opinion Accompanying the Partial Search Result, PCT/US2017/061038 (Methods and Systems for Synthetic Computed Tomography (CT) Image Creation, filed Nov. 10, 2017), ISA/EPO, 5 pages, dated Feb. 27, 2018.
International Search Report, PCT/US17/61032 (Synthetic Computed Tomography (CT) Image Creation Using a Generalized Registration Error (GRE) Metric, filed Nov. 10, 2017), issued by ISA/EPO, 6 pages, dated May 7, 2018.
International Search Report, PCT/US2017/061038 (Methods and Systems for Synthetic Computed Tomography (CT) Image Creation, filed Nov. 10, 2017), ISA/EPO, 6 pages, dated Apr. 19, 2018.
Uh, J. et al., MRI-based treatment planning with pseudo CT generated through atlas registration, Medical Physics, 41(5):051711-1-051711-8 (2014).
Written Opinion, PCT/US17/61032 (Synthetic Computed Tomography (CT) Image Creation Using a Generalized Registration Error (GRE) Metric, filed Nov. 10, 2017), issued by ISA/EPO, 11 pages, dated May 7, 2018.
Written Opinion, PCT/US2017/061038 (Methods and Systems for Synthetic Computed Tomography (CT) Image Creation, filed Nov. 10, 2017), ISA/EPO, 9 pages, dated Apr. 19, 2018.

\* cited by examiner

METHODS AND SYSTEMS FOR SYNTHETIC COMPUTED TOMOGRAPHY (CT) IMAGE CREATION

CROSS REFERENCE TO RELATED APPLICATION

The application is a 371 National Stage entry of International Application No. PCT/US2017/061038, which claims the benefit of U.S. Application Ser. No. 62/469,140 filed on Mar. 9, 2017, the disclosures of each of which are hereby incorporated by reference in their entireties. This application also claims the benefit of U.S. Application Ser. No. 62/420,499 filed on Nov. 10, 2016 and U.S. Application Ser. No. 62/445,937 filed on Jan. 13, 2017.

GOVERNMENT SUPPORT

This invention was made with government support under CA008748 awarded by the National Institutes of Health. The government has certain rights in the invention.

TECHNICAL FIELD

This invention relates generally to methods and systems of in vivo biological imaging (e.g. clinical and/or research). More particularly, in certain embodiments, the invention relates to systems and methods for generating synthetic computed tomography (CT) images from magnetic resonance images (MRI).

BACKGROUND

Radiation therapy planning for cancer treatment may require that a patient undergo both a magnetic resonance (MR) imaging scan and a computed tomography (CT) scan. MR imaging has high soft tissue contrast for accurate visualization of areas for radiation treatment, while CT imaging provides electron density information that is needed for performing adequate dose calculations. The MR and CT scans are registered, the areas for radiation treatment are visualized, a dose plan is determined, and the radiotherapy is carried out.

It can be expensive and time consuming for a patient to undergo both MR and CT scanning. In addition, the act of registration of the MR and CT scans can introduce inaccuracies into the radiation therapy planning process. Thus, it is advantageous to produce synthetic CT scans from actual MR scans, thereby allowing the patient to only undergo MR scanning for purposes of radiation therapy planning, rather than both MR and CT scanning.

Previous methods of generating synthetic CTs use either bulk assignment of Hounsfield units (or density) based on clustering of general tissue types (e.g., muscle, bone), or they use atlas-based methods. However, previous methods lack accurate assignment of the Hounsfield unit to each point in the synthetic CT.

Visualization and manual segmentation of the normal tissues of a patient's CT or MR images is a time consuming process. Thus, it is advantageous to automatically segment these tissues using atlas-based methods. However, previous methods may lack accurate definition of the normal tissues in the patient's images.

SUMMARY OF THE INVENTION

Presented herein are systems and methods for synthetic CT image creation that allow MR-only radiotherapy of cancer patients, e.g., head and neck (H&N) cancer patients, prostate cancer patients, patients with cancer of the pelvis, abdomen cancer patients, patients with cancer of the extremities, brain cancer patients, or thorax cancer patients. Also presented are methods of automatic segmentation of normal tissue in CT or MR images of cancer patients. Furthermore, the methods and systems described herein also feature image processing techniques that improve the similarity between CT and MR images prior to CT-MR image registration, as well as standardization of the MR intensity histograms prior to MR-MR registration. Application of the techniques result in more accurate assignment of the Hounsfield unit to each point in the synthetic CT compared to other atlas-based methods, providing for more accurate dosing in MR-only radiotherapy simulation and planning. Furthermore, application of the same techniques can result in more accurate transfer of normal tissue segmentations between MR or CT image pairs.

In certain embodiments, the technique relies on a multi-modality atlas of registered CT and MR images from a representative population of previously imaged patients. For any new patient, the atlas MR images are first deformably registered to the new patient's MR images. Once the MR images of the new patient are registered to the atlas MRs, data from the co-registered atlas CT images are used to generate a synthetic CT image for the new patient. In certain embodiments, the synthetic CT image intensity value at each point is a weighted average of the intensity values from each of the atlas CT images. In the experimental example described herein, for example, the RMS error in intensity value of the synthetic CT was found to be 124 Hounsfield units (HU) in a study of twelve routine H&N cancer patients.

In one aspect, the invention is directed to a method for creating one or more synthetic computed tomography (CT) images (e.g., 2D and/or 3D images) for a subject, the method comprising the steps of: accessing (e.g., acquiring) one or more magnetic resonance (MR) images of the subject; deformably registering, by a processor of a computing device, each of the one or more MR images of the subject to one or more atlas MR images to produce one or more MR-MR registered images for the subject, wherein the one or more atlas MR images are one or more MR images from a representative population of previously imaged subjects, the one or more atlas MR images having one or more corresponding co-registered (e.g., actual) atlas CT images; and generating, by the processor, the one or more synthetic CT images for the subject using i) the one or more MR-MR registered images for the subject, and ii) one or more of the co-registered atlas CT images.

In certain embodiments, the one or more synthetic CT images comprise 3D images.

In certain embodiments, the method comprises displaying, by the processor, the one or more synthetic CT images.

In certain embodiments, the one or more co-registered atlas CT images are each registered to a standardized atlas MR image from the representative population using a rigid+deformable registration to construct an atlas of CT-MR, then used to generate the synthetic CT image for the subject. In certain embodiments, bone intensity in each of the atlas CT images are suppressed in creating the CT-MR atlas, thereby improving registration of the CT-MR atlas.

In certain embodiments, the method comprises determining, by the processor, a radiotherapy dose plan using the one or more synthetic computed tomography (CT) images for the subject (and, optionally, using the one or more MR images for the subject). In certain embodiments, the method comprises administering the radiotherapy dose plan to the subject.

In certain embodiments, the one or more synthetic computed tomography (CT) images are H&N (Head and Neck) images. In certain embodiments, the method further comprises determining, by the processor, a radiotherapy dose plan for treatment of H&N cancer in the subject.

In certain embodiments, the one or more synthetic CT images comprise images of the prostate and/or the pelvis of the subject. In certain embodiments, the method further comprises determining, by the processor, a radiotherapy dose plan for treatment of prostate cancer and/or cancer of the pelvis in the subject.

In certain embodiments, the one or more synthetic CT images comprise images of the abdomen of the subject. In certain embodiments, the method further comprises determining, by the processor, a radiotherapy dose plan for treatment of cancer of the abdomen in the subject.

In certain embodiments, the one or more synthetic CT images comprise images of the extremities of the subject. In certain embodiments, the method further comprises determining, by the processor, a radiotherapy dose plan for treatment of cancer of the extremities in the subject.

In certain embodiments, the one or more synthetic CT images comprise images of the brain of the subject. In certain embodiments, the method further comprises determining, by the processor, a radiotherapy dose plan for treatment of cancer of the brain in the subject.

In certain embodiments, the one or more synthetic CT images comprise images of the thorax of the subject. In certain embodiments, the method further comprises determining, by the processor, a radiotherapy dose plan for treatment of cancer of the thorax in the subject.

In another aspect, the invention is directed to a system for creating a synthetic computed tomography (CT) image for a subject, the system comprising: a processor; and a memory having instructions stored thereon, wherein the instructions, when executed by the processor, cause the processor to: access (e.g., acquire) one or more magnetic resonance (MR) images of the subject; deformably register, by a processor of a computing device, each of the one or more MR images of the subject to one or more atlas MR images to produce one or more MR-MR registered images for the subject, where the one or more atlas MR images are one or more MR images from a representative population of previously imaged subjects, the one or more atlas MR images having corresponding co-registered (e.g., actual) atlas CT images; and generate, by the processor, the synthetic CT image for the subject using i) the one or more MR-MR registered images for the subject, and ii) one or more of the co-registered atlas CT images.

In another aspect, the invention is directed to a method for automated image segmentation of tissues in an atlas MR image or atlas CT image, the method comprising the steps of: automatically segmenting, by a processor of a computing device, an atlas image by clustering the image into classes of air, bone, and soft tissue, and transforming a cluster center of the bone class to the air class to suppress the bone signal and produce a segmented atlas image with tissue contours (e.g., improved contours of normal tissue); accessing (e.g., acquiring) an image of a subject; and deformably registering, by a processor of a computing device, the image of the subject to the segmented atlas image to produce a registered image for the subject with tissue contours. In certain embodiments, the atlas MR image comprises an atlas MR image or atlas CT image. In certain embodiments, the accessed image of the subject comprises a MR image or CT image.

Embodiments described with respect to one aspect of the invention may be, applied to another aspect of the invention (e.g., features of embodiments described with respect to one independent claim are contemplated to be applicable to other embodiments of other independent claims).

DESCRIPTION OF THE INVENTION

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In certain embodiments, administration is oral. Additionally or alternatively, in certain embodiments, administration is parenteral. In certain embodiments, administration is intravenous.

As used herein, the term "cancer" refers to a malignant neoplasm or tumor (Stedman's Medical Dictionary, 25th ed.; Hensly ed.; Williams & Wilkins: Philadelphia, 1990). Exemplary cancers include, but are not limited to head and neck cancers, prostate cancer, cancer of the pelvis, cancer of the abdomen, cancer of the extremities, brain cancer, or thorax cancer.

As used herein, an "image" includes any visual representation, such as a photo, a video frame, streaming video, as well as any electronic, digital or mathematical analogue of a photo, video frame, or streaming video. Any apparatus or system described herein, in certain embodiments, includes a display for displaying an image or any other result produced by the processor. Any method described herein, in certain embodiments, includes a step of displaying an image or any other result produced via the method.

As used herein, "3-D" or "three-dimensional" with reference to an "image" means conveying information about three dimensions. A 3-D image may be rendered as a dataset in three dimensions and/or may be displayed as a set of two-dimensional representations, or as a three-dimensional representation.

As used herein, the term "subject" includes humans and mammals (e.g., mice, rats, pigs, cats, dogs, and horses).

As used herein, the phrase "therapeutic agent" refers to any agent that has a therapeutic effect and/or elicits a desired biological and/or pharmacological effect, when administered to a subject.

As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. In certain embodiments, treatment comprises delivery of therapeutics, including but not limited to, small molecule delivery, radiotherapy, and/or immunotherapy.

BRIEF DESCRIPTION OF DRAWINGS

The foregoing and other objects, aspects, features, and advantages of the present disclosure will become more apparent and better understood by referring to the following description taken in conduction with the accompanying drawings, in which.

EXPERIMENTAL EXAMPLE

Eleven sets of CT and MM (in-phase, Philips mDixon sequence) scans were randomly selected from a pool of H&N cancer patients. A bias field correction algorithm was primarily applied to each MRI scan to eliminate the intensity variation due to B0 and B1 field inhomogeneity and tissue susceptibility effect. A landmark-based MM standardization technique was then used to standardize the MR intensity histograms wherein each landmark, a total of four, corresponds to a different histogram extremum. Using a rigid+ deformable registration, a CT scan from each patient was registered to the standardized MRI to construct an atlas of CT-MRI. To improve the performance of the registration, bone intensity in the CT image was suppressed to increase the image intensity similarity between CT and MRI scans. CT image was initially clustered into classes of air, bone and soft tissue. The cluster center of the bone class was then transformed to the air class to suppress the bone signal. To synthesize CT for a new patient, using the displacement fields achieved by registering each MRI in the atlas to the new patient MM, all CTs from the atlas were also deformed onto the new patient. The synthetic CT value at each point would be a weighted average of the intensity values from each of the atlas CT images. To evaluate the technique, the mean absolute error (MAE) between the synthetic CT and the original CT was computed over the entire CT and air and bone regions in a leave-one-out scheme. The efficiency of the registration scheme was also compared with commercial software.

Results:

MAE between the original and the synthetic CT was 67±9, 114±22, and 116±9 HU for the entire image, air and bone regions, respectively. It was found that the registration strategy described herein lowered the MAE over the entire CT and lowered the MAE of the bone regions. The primary dose calculation revealed highly consistent results between the original and the synthetic CT.

Discussion of Experimental Example:

The multi-atlas based approach described herein was found to be useful for generation of synthetic CT for MR-only radiotherapy of cancer patients, e.g., the head & neck cancer patients whose images were examined. The registration scheme presented herein enhances the performance of the atlas propagation. Table 1 shows an example of dose calculation for a head and neck cancer patient using original and synthetic CT generated by the multi-atlas based algorithm. Numbers are in cGy.

TABLE 1

|  |  | PTV 70 | PTV 66 | PTD 54 | PTV 50 | Parotid R | Parotid L | SMG R | SMG L | Mandible | Brachial Plexus R | Brachial Plexus L | Larynx |
|---|---|---|---|---|---|---|---|---|---|---|---|---|---|
| Original CT | Min | 5526 | 5657 | 2920 | 4026 |  |  |  |  |  |  |  |  |
|  | Max | 6585 | 6613 | 6526 | 5702 |  |  |  |  | 6300 | 5991 | 5270 | 5914 |
|  | Mean | 6306 | 6352 | 5823 | 5206 | 1550 | 2386 | 5791 | 3983 |  |  |  |  |
|  | D95 | 6113 | 6142 | 5482 | 5061 |  |  |  |  |  |  |  |  |
| Synthetic CT | Min | 5479 | 5621 | 3114 | 4180 |  |  |  |  |  |  |  |  |
|  | Max | 6590 | 6685 | 6538 | 5689 |  |  |  |  | 6319 | 5993 | 5280 | 5933 |
|  | Mean | 6307 | 6370 | 5829 | 5211 | 1597 | 2366 | 5811 | 4078 |  |  |  |  |
|  | D95 | 6110 | 6144 | 5488 | 5064 |  |  |  |  |  |  |  |  |

Figure 1:
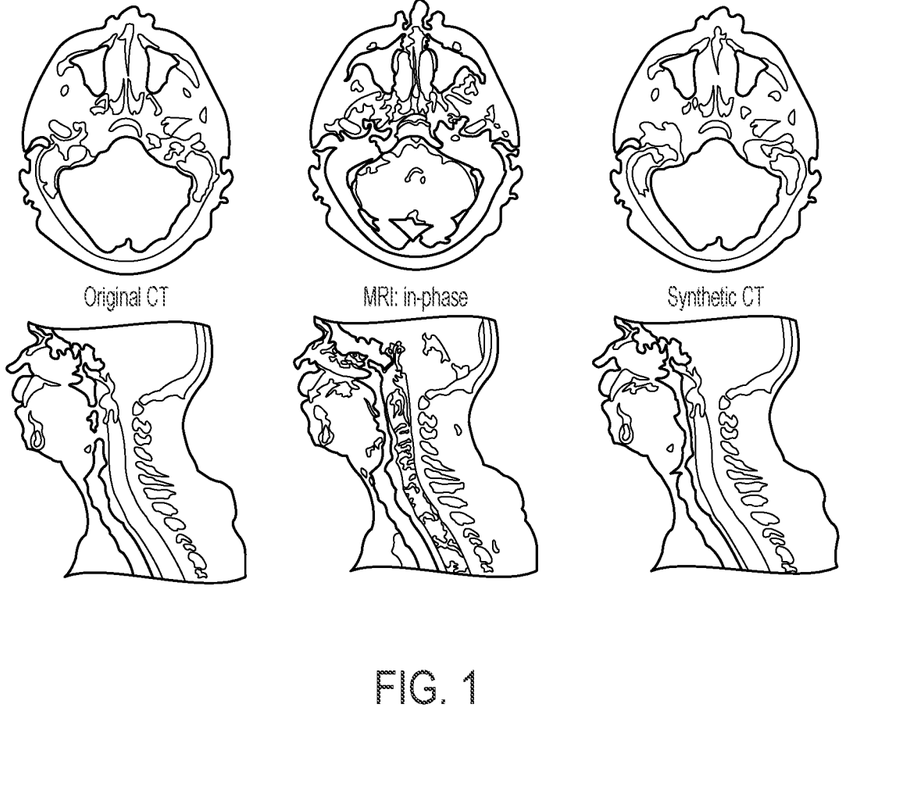
FIG. 1 is an example of the synthetic CT generated by the atlas-based approach described herein: (left panel) Original CT, (middle panel) MM: in phase, (right panel) Synthetic CT.
Figure 2:
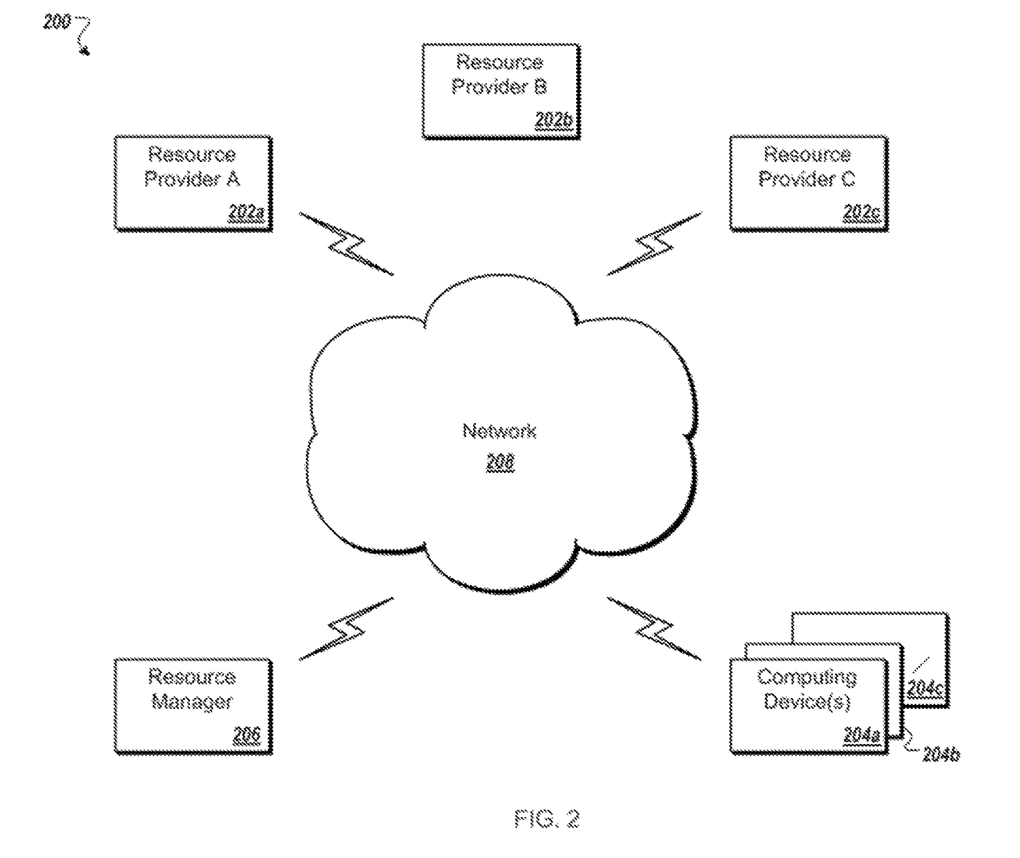
FIG. 2 is a block diagram of an exemplary cloud computing environment, used in certain embodiments.

Networks and Devices for use in the Methods and Systems Described Herein:

As shown in FIG. 2, an implementation of a network environment 200 for use in providing systems, methods, and architectures for retrieving, managing, and analyzing clinical data from a plurality of sources as described herein is shown and described. In brief overview, referring now to FIG. 2, a block diagram of an exemplary cloud computing environment 200 is shown and described. The cloud computing environment 200 may include one or more resource providers 202a, 202b, 202c (collectively, 202). Each resource provider 202 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 202 may be connected to any other resource provider 202 in the cloud computing environment 200. In some implementations, the resource providers 202 may be connected over a computer network 208. Each resource provider 202 may be connected to one or more computing device 204a, 204b, 204c (collectively, 204), over the computer network 208.

The cloud computing environment 200 may include a resource manager 206. The resource manager 206 may be connected to the resource providers 202 and the computing devices 204 over the computer network 208. In some implementations, the resource manager 206 may facilitate the provision of computing resources by one or more resource providers 202 to one or more computing devices 204. The resource manager 206 may receive a request for a computing resource from a particular computing device 204. The resource manager 206 may identify one or more resource providers 202 capable of providing the computing resource requested by the computing device 204. The resource manager 206 may select a resource provider 202 to provide the computing resource. The resource manager 206 may facilitate a connection between the resource provider 202 and a particular computing device 204. In some implementations, the resource manager 206 may establish a connection between a particular resource provider 202 and a particular computing device 204. In some implementations, the resource manager 206 may redirect a particular computing device 204 to a particular resource provider 202 with the requested computing resource.

Figure 3:
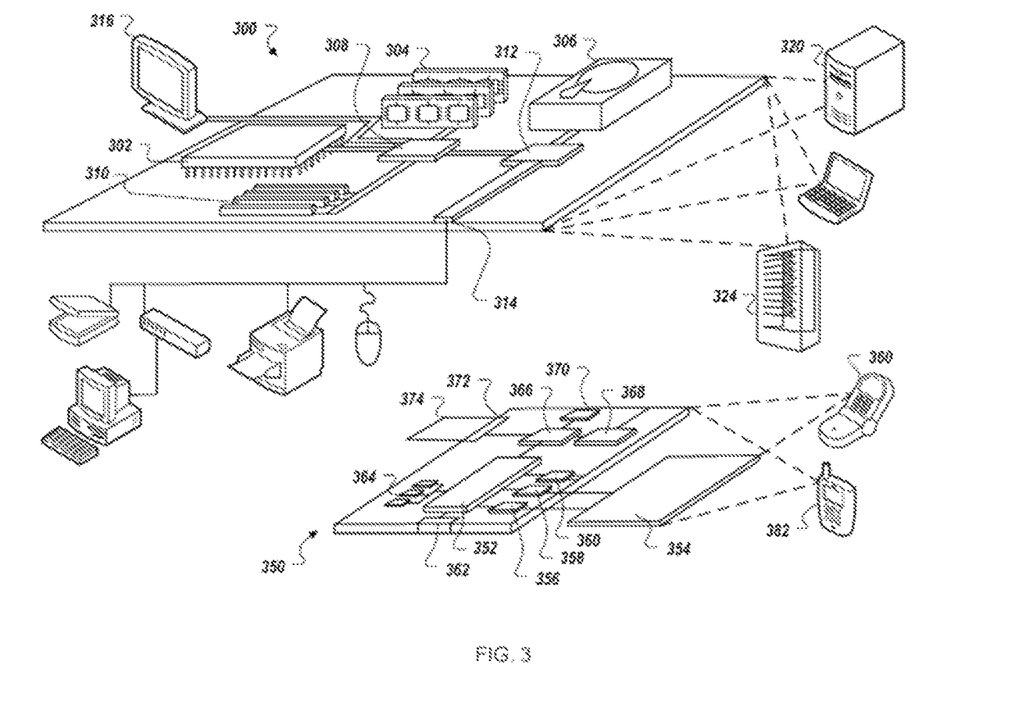
FIG. 3 is a block diagram of an example computing device and an example mobile computing device used in certain embodiments.

FIG. 3 shows an example of a computing device 300 and a mobile computing device 530 that can be used to implement the techniques described in this disclosure. The computing device 300 is intended to represent various forms of digital computers, such as laptops, desktops, workstations, personal digital assistants, servers, blade servers, mainframes, and other appropriate computers. The mobile computing device 530 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 300 includes a processor 302, a memory 304, a storage device 306, a high-speed interface 308 connecting to the memory 304 and multiple high-speed expansion ports 310, and a low-speed interface 312 connecting to a low-speed expansion port 314 and the storage device 306. Each of the processor 302, the memory 304, the storage device 306, the high-speed interface 308, the high-speed expansion ports 310, and the low-speed interface 312, are interconnected using various busses, and may be mounted on a common motherboard or in other manners as appropriate. The processor 302 can process instructions for execution within the computing device 300, including instructions stored in the memory 304 or on the storage device 306 to display graphical information for a GUI on an external input/output device, such as a display 316 coupled to the high-speed interface 308. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 304 stores information within the computing device 300. In some implementations, the memory 304 is a volatile memory unit or units. In some implementations, the memory 304 is a non-volatile memory unit or units. The memory 304 may also be another form of computer-readable medium, such as a magnetic or optical disk.

The storage device 306 is capable of providing mass storage for the computing device 300. In some implementations, the storage device 306 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 302), perform one or more methods, such as those described above. The instructions can also be stored by one or more storage devices such as computer- or machine-readable mediums (for example, the memory 304, the storage device 306, or memory on the processor 302).

The high-speed interface 308 manages bandwidth-intensive operations for the computing device 300, while the low-speed interface 312 manages lower bandwidth-intensive operations. Such allocation of functions is an example only. In some implementations, the high-speed interface 308 is coupled to the memory 304, the display 316 (e.g., through a graphics processor or accelerator), and to the high-speed expansion ports 310, which may accept various expansion cards (not shown). In the implementation, the low-speed interface 312 is coupled to the storage device 306 and the low-speed expansion port 314. The low-speed expansion port 314, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 300 may be implemented in a number of different forms, as shown in the figure. For example, it may be implemented as a standard server 520, or multiple times in a group of such servers. In addition, it may be implemented in a personal computer such as a laptop computer 522. It may also be implemented as part of a rack server system 524. Alternatively, components from the computing device 300 may be combined with other components in a mobile device (not shown), such as a mobile computing device 530. Each of such devices may contain one or more of the computing device 300 and the mobile computing device 530, and an entire system may be made up of multiple computing devices communicating with each other.

The mobile computing device 530 includes a processor 552, a memory 564, an input/output device such as a display 554, a communication interface 566, and a transceiver 568, among other components. The mobile computing device 530 may also be provided with a storage device, such as a micro-drive or other device, to provide additional storage. Each of the processor 552, the memory 564, the display 554, the communication interface 566, and the transceiver 568, are interconnected using various buses, and several of the components may be mounted on a common motherboard or in other manners as appropriate.

The processor 552 can execute instructions within the mobile computing device 530, including instructions stored in the memory 564. The processor 552 may be implemented as a chipset of chips that include separate and multiple analog and digital processors. The processor 552 may provide, for example, for coordination of the other components of the mobile computing device 530, such as control of user interfaces, applications run by the mobile computing device 530, and wireless communication by the mobile computing device 530.

The processor 552 may communicate with a user through a control interface 558 and a display interface 556 coupled to the display 554. The display 554 may be, for example, a TFT (Thin-Film-Transistor Liquid Crystal Display) display or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may provide communication with the processor 552, so as to enable near area communication of the mobile computing device 530 with other devices. The external interface 562 may provide, for example, for wired communication in some implementations, or for wireless communication in other implementations, and multiple interfaces may also be used.

The memory 564 stores information within the mobile computing device 530. The memory 564 can be implemented as one or more of a computer-readable medium or media, a volatile memory unit or units, or a non-volatile memory unit or units. An expansion memory 574 may also be provided and connected to the mobile computing device 530 through an expansion interface 572, which may include, for example, a SIMM (Single In Line Memory Module) card interface. The expansion memory 574 may provide extra storage space for the mobile computing device 530, or may also store applications or other information for the mobile computing device 530. Specifically, the expansion memory 574 may include instructions to carry out or supplement the processes described above, and may include secure information also. Thus, for example, the expansion memory 574 may be provide as a security module for the mobile computing device 530, and may be programmed with instructions that permit secure use of the mobile computing device 530. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 552), perform one or more methods, such as those described above. The instructions can also be stored by one or more storage devices, such as one or more computer- or machine-readable mediums (for example, the memory 564, the expansion memory 574, or memory on the processor 552). In some implementations, the instructions can be received in a propagated signal, for example, over the transceiver 568 or the external interface 562.

The mobile computing device 530 may communicate wirelessly through the communication interface 566, which may include digital signal processing circuitry where necessary. The communication interface 566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 568 using a radio-frequency. In addition, short-range communication may occur, such as using a Bluetooth®, Wi-Fi™, or other such transceiver (not shown). In addition, a GPS (Global Positioning System) receiver module 570 may provide additional navigation- and location-related wireless data to the mobile computing device 530, which may be used as appropriate by applications running on the mobile computing device 530.

The mobile computing device 530 may also communicate audibly using an audio codec 560, which may receive spoken information from a user and convert it to usable digital information. The audio codec 560 may likewise generate audible sound for a user, such as through a speaker, e.g., in a handset of the mobile computing device 530. Such sound may include sound from voice telephone calls, may include recorded sound (e.g., voice messages, music files, etc.) and may also include sound generated by applications operating on the mobile computing device 530.

The mobile computing device 530 may be implemented in a number of different forms, as shown in the figure. For example, it may be implemented as a cellular telephone 580. It may also be implemented as part of a smart-phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/ or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the modules (e.g., a data aggregation module, a mapping module, a specifications module) described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for creating a synthetic computed tomography (CT) image for a subject, the method comprising the steps of:
    accessing a magnetic resonance (MR) image of the subject;
    deformably registering, by a processor of a computing device, each of a plurality of atlas MR images to the MR image of the subject to produce MR-MR displacement fields, wherein the plurality of atlas MR images are MR images from a representative population of previously imaged subjects, each of the plurality of atlas MR images having a corresponding co-registered atlas CT image; and
    generating, by the processor, the synthetic CT image for the subject using i) the MR-MR displacement fields, and ii) the co-registered atlas CT images, wherein the co-registered atlas CT images are each registered to a standardized atlas MR image from the representative population using a rigid+deformable registration to construct an atlas of CT-MR, then used to generate the synthetic CT image for the subject, wherein bone intensities in each of the atlas CT images are suppressed in creating the CT-MR atlas, thereby improving registration of the CT-MR atlas.

2. The method of claim 1, wherein the synthetic CT image is a 3D image.

3. The method of claim 1, further comprising displaying, by the processor, the synthetic CT image.

4. The method of claim 1, further comprising determining, by the processor, a radiotherapy dose plan using the synthetic computed tomography (CT) image for the subject.

5. The method of claim 4, further comprising administering the radiotherapy dose plan to the subject.

6. The method of claim 1, wherein the synthetic computed tomography (CT) image is a H&N (Head and Neck) image.

7. The method of claim 6, wherein the method further comprises determining, by the processor, a radiotherapy dose plan for treatment of H&N cancer in the subject.

8. The method of claim 1, wherein the synthetic CT image is an image of the prostate and/or the pelvis of the subject.

9. The method of claim 8, wherein the method further comprises determining, by the processor, a radiotherapy dose plan for treatment of prostate cancer and/or cancer of the pelvis in the subject.

10. The method of claim 1, wherein the synthetic CT image is an image of the abdomen of the subject.

11. The method of claim 10, wherein the method further comprises determining, by the processor, a radiotherapy dose plan for treatment of cancer of the abdomen in the subject.

12. The method of claim 1, wherein the synthetic CT image is an image of the extremities of the subject.

13. The method of claim 12, wherein the method further comprises determining, by the processor, a radiotherapy dose plan for treatment of cancer of the extremities in the subject.

14. The method of claim 1, wherein the synthetic CT image is an image of the brain of the subject.

15. The method of claim 14, wherein the method further comprises determining, by the processor, a radiotherapy dose plan for treatment of cancer of the brain in the subject.

16. The method of claim 1, wherein the synthetic CT image is an image of the thorax of the subject.

17. The method of claim 16, wherein the method further comprises determining, by the processor, a radiotherapy dose plan for treatment of cancer of the thorax in the subject.

18. A system for creating a synthetic computed tomography (CT) image for a subject, the system comprising:
   a processor; and
   a memory having instructions stored thereon, wherein the instructions, when executed by the processor, cause the processor to:
      access a magnetic resonance (MR) image of the subject;
      deformably register, by a processor of a computing device, each of a plurality of atlas MR images to the MR image of the subject to produce MR-MR displacement fields, where the one or more plurality of atlas MR images are MR images from a representative population of previously imaged subjects, each of the plurality of atlas MR images having a corresponding co-registered atlas CT image; and
      generate, by the processor, the synthetic CT image for the subject using i) the MR-MR displacement fields, and ii) the co-registered atlas CT images, wherein the co-registered atlas CT images are each registered to a standardized atlas MR image from the representative population using a rigid+deformable registration to construct an atlas of CT-MR, then used to generate the synthetic CT image for the subject, wherein bone intensities in each of the atlas CT images are suppressed in creating the CT-MR atlas, thereby improving registration of the CT-MR atlas.

19. The method of claim 4, wherein the step of determining, by the processor, the radiotherapy dose plan additionally uses the MR image for the subject.

\* \* \* \* \*